(12) United States Patent
Frassetto et al.

(10) Patent No.: US 9,512,093 B2
(45) Date of Patent: Dec. 6, 2016

(54) PROCESS FOR MANUFACTURING 4-PROPARGYLATED AMINO-BENZOXAZINONES

(71) Applicant: BASF SE, Ludwigshafen (DE)

(72) Inventors: Timo Frassetto, Mannheim (DE);
Maximilian Dochnahl, Munich (DE);
Michael Rack, Eppelheim (DE);
Volker Maywald, Ludwigshafen (DE);
Bernd Wolf, Niederkirchen (DE);
Roland Goetz, Neulussheim (DE);
Philip Muelheims, Mannheim (DE);
Rudolf Haeberle, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/899,755

(22) PCT Filed: Jun. 17, 2014

(86) PCT No.: PCT/EP2014/062695
§ 371 (c)(1),
(2) Date: Dec. 18, 2015

(87) PCT Pub. No.: WO2014/202589
PCT Pub. Date: Dec. 24, 2014

(65) Prior Publication Data
US 2016/0137615 A1   May 19, 2016

(30) Foreign Application Priority Data

Jun. 21, 2013  (EP) .................................... 13173215

(51) Int. Cl.
  *C07D 265/36*  (2006.01)
  *C07C 17/16*  (2006.01)
  *C07D 413/04*  (2006.01)

(52) U.S. Cl.
  CPC ............. *C07D 265/36* (2013.01); *C07C 17/16* (2013.01); *C07D 413/04* (2013.01)

(58) Field of Classification Search
  CPC .................................................. C07D 265/36
  See application file for complete search history.

(56) References Cited

U.S. PATENT DOCUMENTS 6,291,731 B1   9/2001   Stamm et al.

FOREIGN PATENT DOCUMENTS

| EP | 0387531 | 9/1990 |
|----|---------|--------|
| WO | WO 9946226 | 9/1999 |
| WO | WO 2010145992 | 12/2010 |
| WO | WO 2013092856 | 6/2013 |
| WO | WO 2013092859 | 6/2013 |
| WO | WO 2014026893 | 2/2014 |

OTHER PUBLICATIONS

European Search Report, issued in Application No. 13173215.8, dated Oct. 11, 2013.
International Preliminary Report on Patentability, issued in PCT/EP2014/062695, dated Jun. 8, 2015.
International Search Report, issued in PCT/EP2014/062695, dated Aug. 22, 2014.
Vernon, "Kinetics and Mechanisms of Nucleophilic Displacements in Allylic Systems. Part VIII. The Reactivities of Allylic Chlorides towards Bimolecular Substitute without Rearrangement," Journal of the chemical Society (Resumed), (1954), pp. 4462-4470.

*Primary Examiner* — Kahsay Habte
(74) *Attorney, Agent, or Firm* — Brinks Gilson & Lione

(57) ABSTRACT

The present invention relates to a process for manufacturing 4-propargylated amino-benzoxazinones of formula (I),

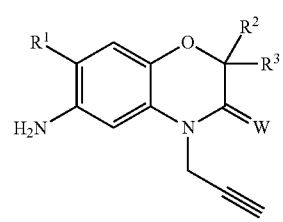

(I)

comprising the following steps:
step a) preparing propargyl chloride by reacting propargyl alcohol with thionyl chloride optionally in the presence of a catalyst; and
step b) reacting the propargyl chloride prepared in step (a) with a NH-benzoxazinone of formula (II);
wherein the variables are defined according to the description.

13 Claims, No Drawings

PROCESS FOR MANUFACTURING 4-PROPARGYLATED AMINO-BENZOXAZINONES

This application is a National Stage application of International Application No. PCT/EP2014/062695, filed Jun. 17, 2014. This application also claims priority under 35 U.S.C. §119 to European Patent Application No. 13173215.8, filed Jun. 21, 2013.

DESCRIPTION

The invention relates a process for manufacturing 4-propargylated amino-benzoxazinones of formula (I), their use in and a process for manufacturing triazinon-benzoxazinones of formula (IV).

Propargyl chloride (3-chloropropyne) is a valuable intermediate which is required for preparing a series of intermediates and electrolysis auxiliaries, but also as a reagent for introducing a propargyl radical in the preparation of active compounds for pharmaceuticals and crop protection.

WO 99/46226 discloses a continuous method for producing propargyl chloride, wherein phosgene is used as chlorinating agent. Phosgene is a highly toxic substance, which needs extensive safety measures. Further it is necessary to separate the excess of phosgene from the desired propargyl chloride to be able to use the same in subsequent propargylation reactions. This separation can for example be accomplished by extensive distillation via stripping column.

Accordingly, there is still room for improvement, specifically in view of economical, safety and ecological aspects.

WO 2010/145992 discloses a process for the preparation of amino-benzoxazinones by first alkylation of the 4-position of nitro-benzoxazinones and then subsequent reduction of the nitro substituent.

One task of the invention is to provide an improved process for manufacturing 4-propargylated amino-benzoxazinones of formula (I) avoiding extensive preparation, purification, transport and/or storage of propargyl chloride.

Another task of the invention is to provide an improved process for manufacturing triazinon-benzoxazinones of formula (IV).

Surprisingly it has been found that propargyl chloride obtained by reacting propargyl alcohol with thionyl chloride in the presence of a catalyst can directly be used in the preparation of 4-propargylated amino-benzoxazinones of formula (I) without further purification.

Neither by-products, which are dissolved in the propargyl chloride (like e.g. HCl and $SO_2$), nor remaining thionyl chloride do interfere with the propargylation step (b).

Further, it has been found that benzoxazinones bearing at least one halogen atom in the 2-position and a free amino group in the 6-position can be propargylated in the 4-position of the benzoxazinone ring.

The corresponding 4-propargylated amino-benzoxazinones of formula (I) can be obtained in high yields and excellent regioselectivities.

The process of the invention also opens up the possibility to reduce the nitro group prior to introducing the substituent in the 4-position.

Hence, the present invention allows for more flexibility in the synthesis of benzoxazinones since it allows the introduction of substituents that are incompatible with reaction conditions under which an aromatic nitro group is converted into the corresponding amino group.

Accordingly, the present invention relates to a process for manufacturing 4-propargylated amino-benzoxazinones of formula (I),

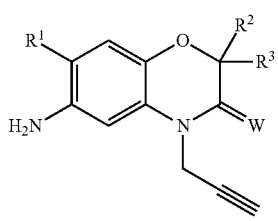

(I)

wherein
$R^1$ is H or halogen;
$R^2$ is halogen;
$R^3$ is H or halogen; and
W is O or S;
which comprises the following steps:
(a) preparing propargyl chloride

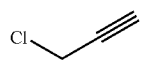

by reacting propargyl alcohol

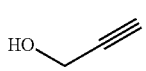

with thionyl chloride optionally in the presence of a catalyst; and
(b) reacting the propargyl chloride prepared in step (a) with a NH-benzoxazinone of formula (II),

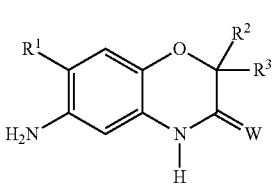

(II)

or a salt thereof,
wherein $R^1$, $R^2$, $R^3$ and W are defined as in formula (I); optionally in the presence of a base.

In a further aspect of the invention there is provided a process for preparing triazinon-benzoxazinones of formula (IV),

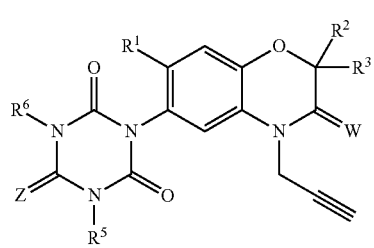

(IV)

wherein $R^1$, $R^2$, $R^3$ and W are defined as in formula (I);
$R^5$ is H, $NH_2$, $C_1$-$C_6$-alkyl or $C_3$-$C_6$-alkynyl;
$R^6$ is H or $C_1$-$C_6$-alkyl; and
Z is O or S.

In a further aspect of the invention there is provided the use of 4-propargylated amino-benzoxazinones of formula (I) in manufacturing triazinon-benzoxazinones of formula (IV).

The process of the invention gives 4-propargylated amino-benzoxazinones of formula (I) in excellent yields, and thus, can be used in the synthesis of triazinon-benzoxazinones of formula (IV) in high yields and purities.

The NH-benzoxazinones of formula (II) as described herein can also be employed in the form of their salts. Suitable are, in general, those salts of the NH-benzoxazinone of formula (II), which cations have no adverse effect on the reaction.

Preferred cations are the ions of the alkali metals, preferably of lithium, sodium, potassium, rubidium and cesium, of the alkaline earth metals, preferably of magnesium, calcium and barium, of the transition metals, preferably of titanium, manganese, iron, copper, silver and zinc, and of the elements boron, aluminum and tin.

Especially preferred the NH-benzoxazinones of formula (II) as described herein are employed in form of their alkali metal or alkaline metal salts.

Particular preference is given to the cations of alkali metals, preferably lithium, sodium and potassium.

The organic moieties mentioned in the definition of the variables according to the present invention, e.g. $R^1$ to $R^6$ are—like the term halogen—collective terms for individual enumerations of the individual group members.

The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$ n-butyl, $CH(CH_3)$—$C_2H_5$, $CH_2$—CH $(CH_3)_2$ and $C(CH_3)_3$;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

The preferred embodiments of the invention mentioned herein below have to be understood as being preferred either independently from each other or in combination with one another.

According to a preferred embodiment of the invention preference is also given to the preparation of those 4-propargylated amino-benzoxazinones of formula (I), wherein the variables, either independently of one another or in combination with one another, have the following meanings:

$R^1$ is preferably H or F; particularly preferred H;

is also preferably halogen, particularly preferred F or Cl, especially preferred F;

$R^2$ is preferably Cl or F, particularly preferred F;

$R^3$ is preferably H, Cl or F, particularly preferred H or F, especially preferred H;

is also preferably halogen, particularly preferred F or Cl, especially preferred F;

W is preferably O, is also preferably S.

Particular preference is also given to the preparation of 4-propargylated amino-benzoxazinones of formula (I.a), which correspond to 4-propargylated amino-benzoxazinones of formula (I) wherein $R^2$ is F and W is O:

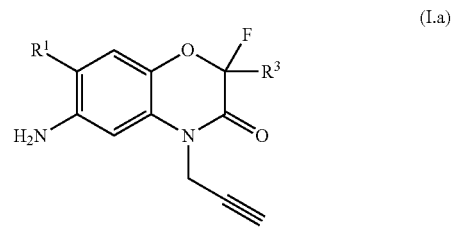

(I.a)

wherein the variables $R^1$ and $R^3$ have the meanings, in particular the preferred meanings, as defined above;

most preference to the preparation of 4-propargylated amino-benzoxazinones of formulae (I.a.1) to (I.a.7) of Table A listed below, in which the variables $R^1$ and $R^3$ together have the meanings given in one row of Table A (4-propargylated amino-benzoxazinones of formulae I.a.1 to I.a.7); and where the definitions of the variables $R^1$ and $R^3$ are of particular importance for the process and the compounds according to the invention not only in combination with one another but in each case also on their own:

TABLE A

| No. | $R^1$ | $R^3$ |
| --- | --- | --- |
| I.a.1. | H | H |
| I.a.2. | H | F |
| I.a.3. | F | H |
| I.a.4. | F | F |
| I.a.5. | F | F |
| I.a.6. | Cl | H |
| I.a.7. | Cl | F |

Very particular preference is given to the preparation of the 4-propargylated amino-benzoxazinone of formula (I.a.5) as defined above:

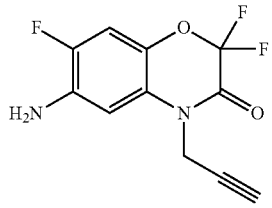

(I.a.5)

The propargyl chloride is prepared by reacting propargyl alcohol with thionyl chloride optionally in the presence of a catalyst.

The reaction of propargyl alcohol with thionyl chloride is usually carried out at from 0° C. to the boiling point of the reaction mixture, preferably from 30° C. to 70° C., particularly preferably from 40° C. to 50° C.

In one embodiment of the process according to the invention, the propargyl alcohol and optionally the catalyst are initially charged in a reaction vessel, if appropriate with the desired solvent, and subsequently the thionyl chloride is added, more preferably is added a little at a time, into the reaction vessel.

In another embodiment of the process according to the invention, the thionyl chloride and optionally the catalyst are initially charged in a reaction vessel, if appropriate with the desired solvent, and subsequently the propargyl alcohol is added, more preferably is added a little at a time, into the reaction vessel.

Step (a) of the process according to the invention is carried out optionally in the presence of a catalyst, i.e. the presence of a catalyst in step (a) is not mandatory.

In one embodiment of the invention step (a) is carried out in the absence of a catalyst.

In another embodiment of the invention, step (a) is carried out in the presence of a catalyst.

As catalyst for the reaction, it is possible to use all suitable catalysts. The catalyst is preferably selected from the group consisting of phosphine oxides, guanidinium salts, open-chain and cyclic alkylureas, alkylacetamides and N,N-dialkylformamides and also mixtures thereof.

The catalyst is preferably selected from at least one of formamides of formula (X) or ureas of formula (XI)

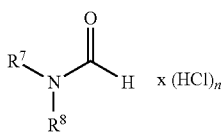

(X)

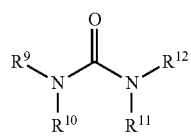

(XI)

wherein
$R^7$, $R^8$, $R^9$, $R^{10}$, $R^{11}$ and $R^{12}$ independently of one another are $C_1$-$C_6$-alkyl, or
$R^7$ and $R^8$, $R^9$ and $R^{10}$, $R^{10}$ and $R^{11}$, or $R^{11}$ and $R^{12}$ independently of one another together form a $C_4$-$C_5$-alkylene chain, each of which may be interrupted by from 1 to 4 oxygen or nitrogen atoms; and
n has a mean value of from 0 to 3.

According to a preferred embodiment of the invention preference is also given to catalysts selected from at least one of formamides of formula (X) or ureas of formula (XI), wherein the variables, either independently of one another or in combination with one another, have the following meanings:

$R^7$ and $R^8$ are preferably $C_2$-$C_6$-alkyl;
 particularly preferably $C_3$-$C_5$-alkyl;
 or together form a $C_4$-$C_5$-alkylene chain, each of which may be interrupted by from 1 or 2 oxygen or nitrogen atoms;
 also particularly preferably are identical radicals selected from among n-butyl and isobutyl;
n has a mean value of from 0 to 3,
 preferably from 0.5 to 2.5,
 in particular from 1 to 2;
$R^9$, $R^{10}$, $R^{11}$ and $R^{12}$ are preferably $C_1$-$C_4$-alkyl,
 particularly preferred selected from methyl or ethyl;
 or $R^9$ and $R^{10}$, $R^{10}$ and $R^{11}$, or $R^{11}$ and $R^{12}$, independently of one another together form a $C_4$-$C_5$-alkylene chain, each of which may be interrupted by from 1 or 2 oxygen or nitrogen atoms.

In one embodiment of the invention the catalyst is mixture comprising at least one formamide of formula (X) and at least one urea of formula (XI), wherein the substituents are as defined above.

In another embodiment the catalyst is preferably at least one formamide of formula (X)

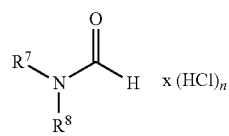

(X)

wherein
$R^7$ and $R^8$ are, independently of one another, $C_1$-$C_6$-alkyl,
 preferably $C_2$-$C_6$-alkyl;
 particularly preferably $C_3$-$C_5$-alkyl;
 or together form a $C_4$-$C_5$-alkylene chain, each of which may be interrupted by from 1 to 4, preferably 1 or 2, oxygen or nitrogen atoms; and
n has a mean value of from 0 to 3,
 preferably from 0.5 to 2.5,
 in particular from 1 to 2.
$R^7$ and $R^8$ are particularly preferably identical radicals selected from among n-butyl and isobutyl.

Particular preference is given to using diisobutylformamide as catalyst.

In general, the pure formamide of formula (X) is introduced into the reaction mixture in which the HCl adduct is generated during the formation of the propargyl chloride.

In another embodiment of the invention the catalyst preferably at least one urea of formula (XI)

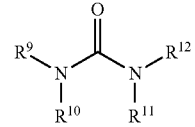

(XI)

wherein
$R^9$, $R^{10}$, $R^{11}$ and $R^{12}$ independently of one another are $C_1$-$C_6$-alkyl,
 preferably $C_1$-$C_4$-alkyl;

particularly preferred selected from methyl or ethyl; or
R⁷ and R⁸, R⁹ and R¹⁰, R¹⁰ and R¹¹, or R¹¹ and R¹²
independently of one another together form a C₄-C₅-
alkylene chain, each of which may be interrupted by
from 1 to 4, preferably 1 or 2, oxygen or nitrogen
atoms.

The amount of catalyst used is usually from 0.1 to 10 mol %;
preferably from 1 to 5 mol %;
particularly preferably from 2 to 3.5 mol %;
based on the amount of alcohol of formula (XI).

In one embodiment of the process according to the invention, the propargyl alcohol is used in excess with regard to the thionyl chloride.

In another embodiment of the process according to the invention, the propargyl alcohol and the halogenating agent are used in equimolar amounts.

In another embodiment of the process according to the invention, the thionyl chloride is used in excess with regard to the propargyl alcohol.

Preferably the molar ratio of the propargyl alcohol to the thionyl chloride is in the range from 1.5:1 to 0.9:1, preferably 1.1:1 to 0.9:1.

The reaction can be carried out in the presence of an inert diluent. Suitable in principle are all solvents which are capable of dissolving the propargyl alcohol and the thionyl chloride at least partly and preferably fully under reaction conditions.

The diluent is preferably used in an amount of from 100 to 400% by weight, particularly preferably from 150 to 250% by weight, based on the amount of propargyl alcohol used.

Examples of suitable solvents are aliphatic hydrocarbons such as pentane, hexane, cyclohexane and mixtures of C₅-C₈-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, esters such as ethyl acetate and butyl acetate; ketones such as acetone, methyl ethyl ketone, diethyl ketone, tert-butyl methyl ketone, cyclohexanone;

Preferred solvents are aromatic hydrocarbons as defined above.

More preferred solvents are toluene and xylene isomer mixtures and also mixtures thereof.

The term solvent as used herein also includes mixtures of two or more of the above compounds.

The end of the reaction can easily be determined by the skilled worker by means of routine methods.

After completion or partial completion of the reaction, the resulting solution can be used as obtained. A work-up is not necessary before transfer of the obtained propargyl chloride into step (b). Preferably the propargyl chloride prepared in step (a) is used directly in step (b) without further purification.

Nevertheless if a purification is desired, the reaction mixture can be worked up by the methods customary for the purpose by means of standard techniques. Examples thereof include distillation, rectification and stripping of dissolved gases.

With respect to the variables within the NH-benzoxazinones of formula (II) necessary for step (b) of the process according to the invention, the particularly preferred embodiments of the NH-benzoxazinones of formula (II)

correspond, either independently of one another or in combination with one another, to those of the variables of R¹, R², R³ and W of formula (I).

Particular preference is also given to the NH-benzoxazinones of formula (II.a) (corresponds to formula (II) wherein R² is F and W is O),

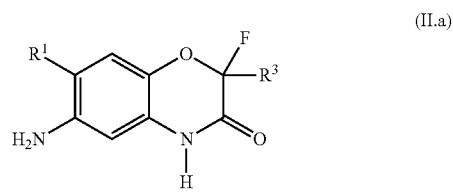

(II.a)

wherein the variables R¹ and R³ have the meanings, in particular the preferred meanings, as defined above; most preference to the NH-benzoxazinones of formulae (II.a.1) to (II.a.6) of Table B listed below, in which the variables R¹ and R³ together have the meanings given in one row of Table B (NH-benzoxazinones of formulae II.a.1 to II.a.6); and where the definitions of the variables R¹ and R³ are of particular importance for the process and the compounds according to the invention not only in combination with one another but in each case also on their own:

TABLE B

| No. | R¹ | R³ |
|---|---|---|
| II.a.1. | H | H |
| II.a.2. | H | F |
| II.a.3. | F | H |
| II.a.4. | F | F |
| II.a.5. | Cl | H |
| II.a.6. | Cl | F |

Very particular preference is given to the NH-benzoxazinone of formula (II.a.4) as defined above:

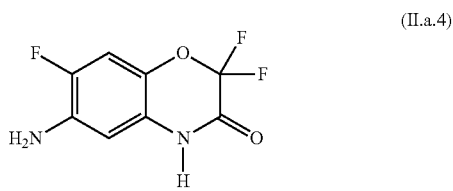 [SMILES: Nc1cc2c(cc1F)OC(F)(F)C(=O)N2]

(II.a.4)

In one preferred embodiment of the invention the NH-benzoxazinone of formula (II) is employed.

In another preferred embodiment of the invention a salt of the NH-benzoxazinone of formula (II) is employed.

The NH-benzoxazinone of formula (II) necessary for the process according to the invention can be prepared as described further below.

Preferably the NH-benzoxazinone of formula (II) or a salt thereof is used in sub-stoichiometric amount with regard to the propargyl chloride. Particularly preferred the molar ratio of the NH-benzoxazinone of formula (II) or a salt thereof to the propargyl chloride is in the range from 1:1 to 1:2, preferred from 1:1 to 1:1.3, especially preferred from 1:1 to 1:1.1, more preferably 1:1.1, also more preferred 1:1.

In one preferred embodiment of the invention a salt of the NH-benzoxazinone of formula (II) is employed, and the reaction of the salt of the NH-benzoxazinone of formula (II)

with the propargyl chloride is carried out in the absence of a base.

In another preferred embodiment of the invention the NH-benzoxazinone of formula (II) is employed, and the reaction of the NH-benzoxazinone of formula (II) with the propargyl chloride is carried out in the presence of a base.

Examples of suitable bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such sodium, potassium or magnesium alkoxides.

Preferred bases are selected from the group consisting of carbonates, hydrogen carbonates, hydroxides, oxides, phosphates and alkoxides.

Preferred bases are selected from the group consisting of carbonates, hydroxides and alkoxides; particularly preferred bases are carbonates.

The term base as used herein also includes mixtures of two or more, preferably two of the above compounds. Particular preference is given to the use of one base.

If a base is employed, preferably the base is used in excess with regard to the NH-benzoxazinone of formula (II).

Particularly preferred the number of base equivalents with regard to the NH-benzoxazinone of formula (II) is in the range from 2:1 to 1:1.1, especially preferred from 1.7:1 to 1:1, more preferably 1.3:1 to 1:1.

Preferably, the reaction of the propargyl chloride with the NH-benzoxazinone of formula (II) and a base or with a salt of the NH-benzoxazinone of formula (II) is carried out in a solvent.

Examples of suitable solvents are dipolar aprotic solvents such as N,N-dimethylformamide (DMF), N,N-dimethylacetamide (DMAC), 1-methyl-2-pyrrolidinone (NMP), 1,3-dimethyl-2-imidazolidinone (DMI), N,N'-dimethylpropylene urea (DMPU), dimethyl sulfoxide (DMSO), acetonitrile, acetone, methyl ethyl ketone, methyl butyl ketone, cyclohexanone, sulfolane, nitromethane; esters such as ethyl acetate; ethers such as dibutylether, tert-butyl methyl ether (TBME), tetrahydrofurane (THF), dioxane; alcohols such as methanol, ethanol, isoproponal, tert-butanol; halogenated hydrocarbons such as chloroform, dichloromethane, dichloroethane, carbon tetrachloride; aliphatic hydrocarbons such as hexanes, cyclohexane; aromatic hydrocarbons such as benzene, toluene, cresols, chlorobenzene.

Preferred solvents include ethyl acetate, N,N-dimethylformamide (DMF) or N,N-dimethyl-acetamide (DMAC).

More preferred solvents include ethyl acetate or N,N-dimethylformamide (DMF).

The term solvent as used herein also includes mixtures of two or more of the above compounds.

The reaction of the propargyl chloride with the NH-benzoxazinone of formula (II) and a base or with a salt of the NH-benzoxazinone of formula (II) is generally carried out at a temperature in the range from 0 to 150° C., preferably in the range from 20 to 100° C., more preferably in the range of from 50 to 85° C.

After completion or partial completion of the reaction, the respective mixture can be worked up by means of standard techniques. Examples thereof include filtration, aqueous work-up, evaporation of solvents and/or other volatile compounds. These methods can also be combined with each other.

In one preferred embodiment the reaction mixture is brought to room temperature and subjected to an aqueous work-up. The organic phase can be dried, e.g. by azeotropic distillation.

In one embodiment the crude product is purified, for example by crystallization, recrystallization or column chromatography.

In another embodiment the crude product is used without further purification.

The purity of the 4-propargylated amino-benzoxazinone (I) is preferably at least 95%, more preferably at least 98%, determined by HPLC, if compound (I) is isolated and not used as a solution in the following step.

4-Propargylated amino-benzoxazinones of formula (I) are useful in the synthesis of triazinon-benzoxazinones of formula (IV):

Triazinon-benzoxazinones of formula (IV) can be prepared by reacting 4-propargylated amino-benzoxazinones of formula (I) with 1,1'-carbonyldiimidazole (CDI) and a (thio)urea compound of formula (V):

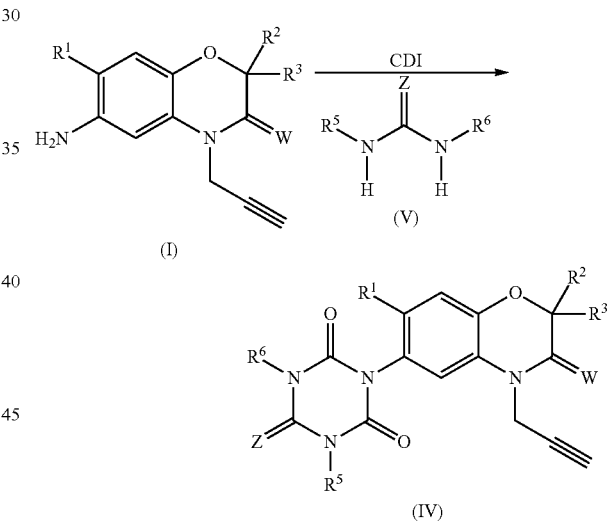

wherein
$R^1$, $R^2$, $R^3$, $R^5$, $R^6$, W and Z are defined as in formula (IV) above.

Preferably, the reaction of the 4-propargylated amino-benzoxazinone of formula (I) with 1,1'-carbonyldiimidazole (CDI) and the (thio)urea compound of formula (V) to obtain the triazinon-benzoxazinone of formula (IV) is carried out in the presence of a base.

Accordingly, in a further preferred embodiment of the process of the invention triazinon-benzoxazinones of formula (IV) are obtained by (a) reacting propargyl alcohol with thionyl chloride in the presence of a catalyst to obtain propargyl chloride;

(b) reacting the propargyl chloride obtained in step (a) with a NH-benzoxazinone of formula (II),

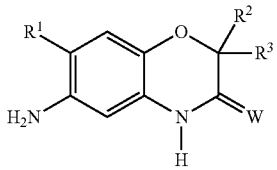
(II)

wherein $R^1$, $R^2$, $R^3$ and W are defined as above;
with a base to obtain the 4-propargylated amino-benzoxazinone of formula (I)

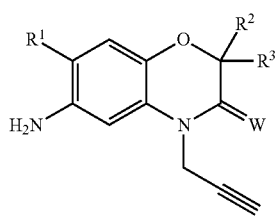
(I)

wherein $R^1$, $R^2$, $R^3$ and W are defined as above;
and (c) reacting the 4-propargylated amino-benzoxazinone of formula (I) with 1,1'-carbonyldiimidazole (CDI) and a (thio)urea compound of formula (V) to obtain the triazinon-benzoxazinone of formula (IV).

In another embodiment of the process according to the invention, the 4-propargylated amino-benzoxazinone of formula (I) is further converted into a triazinon-benzoxazinone of formula (IV),

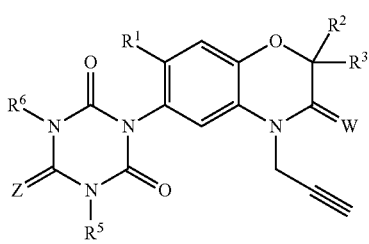
(IV)

wherein
$R^1$ is H or halogen;
$R^2$ is halogen;
$R^3$ is H or halogen;
$R^5$ is H, $NH_2$, $C_1$-$C_6$ alkyl or $C_3$-$C_6$ alkynyl;
$R^6$ is H or $C_1$-$C_6$ alkyl;
W is O or S; and
Z is O or S;
by (c) reacting the 4-propargylated amino-benzoxazinone of formula (I) with 1,1'-carbonyldiimidazole (CDI) and a (thio)urea compound of formula (V),

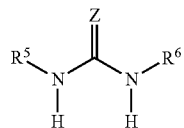
(V)

wherein $R^5$, $R^6$ and Z are defined as in formula (IV);
to obtain the triazinon-benzoxazinone of formula (IV).

In a preferred embodiment step (c) is carried out in the presence of a base.

The NH-benzoxazinones of formula (II) can be prepared by reacting dinitro compounds of formula (VI-1) with a reducing agent to give diamino compounds of formula (VII) and subsequently treating the diamino compounds of formula (VII) with an acid:

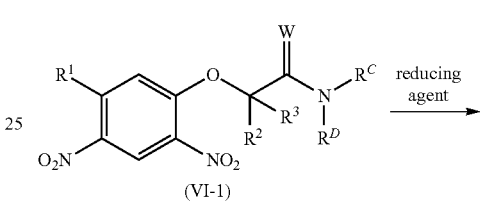
(VI-1)

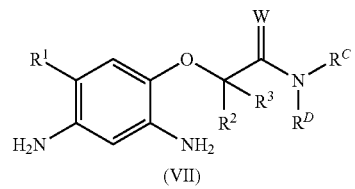
(VII)

↓ acid

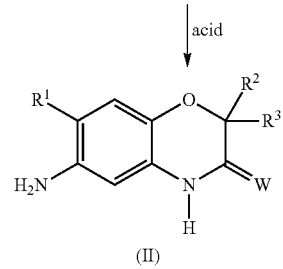
(II)

wherein
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents; and $R^1$, $R^2$, $R^3$ and W are defined as in formula (II) above.

Accordingly, in a further preferred embodiment of the process of the invention the 4-propargylated amino-benzoxazinones of formula (I) are prepared by
(a) reacting a dinitro compound of formula (VI-1) with a reducing agent to obtain a diamino compound of formula (VII);
(b) treating the diamino compound of formula (VII) with an acid to obtain a NH-benzoxazinone of formula (II);
(c) reacting propargyl alcohol with thionyl chloride to obtain propargyl chloride; and and
(d) reacting the propargyl chloride obtained in step (c) with the NH-benzoxazinone of formula (II) obtained in steps (a) and (b) with a base to obtain a 4-propargylated amino-benzoxazinone of formula (I).

The dinitro compounds of formula (VI-1) can be obtained by reacting haloacetamides of formula (VIII) with phenols of formula (IX) in the presence of a base to give aryloxyacetamides of formula (VI) and, if $R^A$ and/or $R^B$ in formula (VI) are H, subsequently treating the aryloxyacetamides of formula (VI) with $HNO_3/H_2SO_4$:

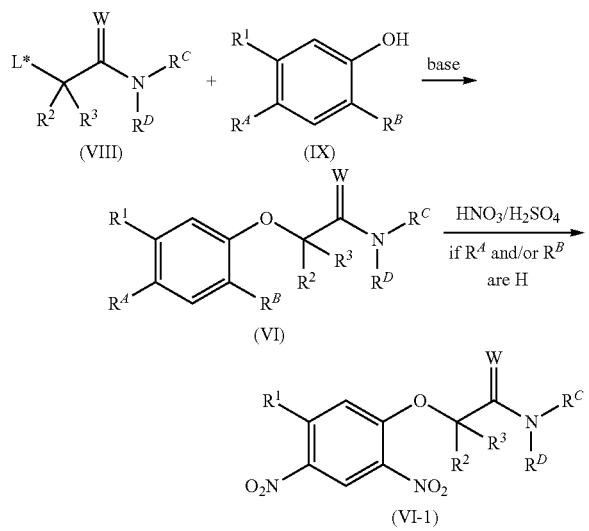

wherein
$R^A$, $R^B$ are independently H or $NO_2$;
L* is halogen;
$R^1$, $R^2$, $R^3$ and W are defined as in formula (II) above; and
$R^C$ and $R^D$ are defined as above.

The phenol of formula (IX) that is converted into the aryloxyacetamide of formula (VI) can also be used in the form of a salt, for example in form of its alkali metal or alkaline metal salt, preferably in the form of its sodium, potassium, magnesium or calcium salt. If a salt of the phenol of formula (IX) is used, the addition of a base is not necessary.

Accordingly, in a further preferred embodiment of the process of the invention the 4-propargylated amino-benzoxazinone of formula (I) are prepared by
(a) reacting an haloacetamide of formula (VIII) with a phenol of formula (IX) in the presence of a base to obtain an aryloxyacetamide of formula (VI);
(b) if $R^A$ and/or $R^B$ in formula (VI) are H:
reacting the aryloxyacetamide of formula (VI) with $HNO_3/H_2SO_4$ to obtain a dinitro compound of formula (VI-1);
(c) reacting the dinitro compound of formula (VI-1) with a reducing agent to obtain a diamino compound of formula (VII);
(d) treating the diamino compound of formula (VII) with an acid to obtain a NH-benzoxazinone of formula (II);
(e) reacting propargyl alcohol with thionyl chloride to obtain propargyl chloride; and
and
(f) reacting the propargyl chloride obtained in step (e) with the NH-benzoxazinone of formula (II) obtained in steps (a) to (d) with a base to obtain a 4-propargylated amino-benzoxazinone of formula (I).

With respect to the variables within the compounds of formulae (IV), (V), (VI), (VI-1), (VII), (VIII) or (IX), the particularly preferred embodiments of the compounds of formulae (IV), (V), (VI), (VI-1), (VII), (VIII) or (IX) correspond, either independently of one another or in combination with one another, to those of the variables of $R^1$, $R^2$, $R^3$ and W of formulae (I) or (II), or have, either independently of one another or in combination with one another, the following meanings:

$R^C$ and $R^D$ preferably are independently of each other $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl,
  wherein the phenyl and the benzyl ring are independently of one another unsubstituted or substituted by 1 to 3 substituents selected from the group consisting of halogen, $C_1$-$C_6$-alkyl or $C_1$-$C_6$-alkoxy,
  or $R^C$ and $R^D$ together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;
particularly preferred are independently of each other $C_1$-$C_4$-alkyl, $C_1$-$C_4$-hydroxyalkyl, $C_1$-$C_6$-alkoxy-$C_1$-$C_4$-alkyl or benzyl,
  wherein the benzyl ring is unsubstituted or substituted by 1 to 3 substituents selected from the group consisting of halogen, $C_1$-$C_4$-alkyl or $C_1$-$C_4$-alkoxy,
  especially preferred the benzyl ring is unsubstituted,
  or $R^C$ and $R^D$ together with the N atom which they are attached to, represent a saturated 5- to 6-membered ring, optionally containing 1 additional oxygen atom, with the ring optionally being substituted with 1 to 2 $C_1$-$C_6$-alkyl substituents;

L* is preferably Cl, Br or I, particularly preferred Cl or Br, especially preferred Br;

$R^5$ is preferably $NH_2$, $C_1$-$C_6$-alkyl or $C_3$-$C_6$-alkynyl; also preferably H or $C_1$-$C_6$-alkyl; more preferably $C_1$-$C_6$-alkyl; most preferably $C_1$-$C_4$-alkyl; particularly preferred $CH_3$;

$R^6$ is preferably $C_1$-$C_6$-alkyl; more preferably $C_1$-$C_4$-alkyl; most preferably $CH_3$;

Z is preferably O,
  is also preferably S.

The invention is illustrated by the following examples without being limited thereto or thereby.

1. PREPARATION OF 4-PROPARGYLATED AMINO-BENZOXAZINONES OF FORMULA (I)

Example 1(a)

Propargyl Chloride

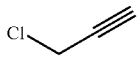

222.7 g thionyl chloride (1.87 mol) were placed in a reaction vessel. 200 g toluene and 6.22 g N,N,N',N'-tetramethyl urea (99%, 53 mmol) have been added consecutively and the solution was heated to 40° C. 100 g propargyl alcohol (99%, 1.77 mol) was added over 40 min with the evolution of gases (HCl, $SO_2$). Stirring at 40° C. was continued for another 2.5 h. The solution was then cooled to ambient temperature and analyzed by GC: mass of solution 370.8 g, 33.4% propargyl chloride corresponding to a yield of 94%.

GCs were recorded on a HP-7890 with the following column: J&W Scientific-60 m DB-624/ID=0.25 mm, FD=1.4 μm.

Method: start temperature at 50° C., ramp 7.5° C./min, end temperature 260° C. for 15 min. propargyl chloride shows a peak at 7.86 min.

Example 1(b)

6-amino-2,2,7-trifluoro-4-(prop-2-ynyl)-1,4-benzoxazin-3-one

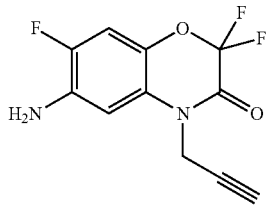 [SMILES: C#CCN1C(=O)C(F)(F)Oc2cc(F)c(N)cc21]

50.0 g 6-amino-2,2,7-trifluoro-4H-1,4-benzoxazin-3-one (99.2%, 0.23 mol), 55 g potassium carbonate (0.40 mol) and 161.5 g DMF were placed in a second reaction vessel at ambient temperature. The suspension was heated to 70° C. 63.4 g propargyl chloride solution (63.4 g, 33.4% (0.28 mol) obtained from example 1(a) were added within 15 min when the inner temperature reached 50° C. The suspension was stirred for another 2 h at 70° C. The mixture was cooled to 50° C. and 39 g aqueous hydrochloric acid (32%) was added during 30 min to control the gas evolution. 614 g water were added and the temperature was brought to 25° C. Stirring was continued for 30 min. The precipitated product was filtered, washed with 50 g water four times and dried in an oven. Yield: 52.8 g 6-amino-2,2,7-trifluoro-4-(prop-2-ynyl)-1,4-benzoxazin-3-one (98.6%, 0.20 mol, yield 89.4%) as an off-white solid.

$^1$H-NMR (500 MHz, DMSO-d6): δ (ppm)=3.45 (s, 1H), 4.74 (s, 2H), 5.42 (s, 2H), 6.85 (d, 1H), 7.26 (d, 1H)

2. PREPARATION OF NH-BENZOXAZINONES OF FORMULA (II)

Example 2.1

6-amino-2,2,7-trifluoro-4H-benzo-[1,4]oxazin-3-one from 2,2-difluoro-2(2,4-dinitro-5-fluoro-phenoxy)]-N,N-dimethyl-acetamide

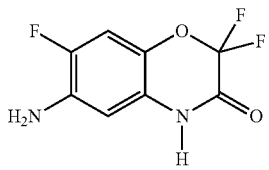 [SMILES: Nc1cc2c(cc1F)OC(F)(F)C(=O)N2]

To a solution of 2,2-difluoro-2-(2,4-dinitro-5-fluoro-phenoxy)-N,N-dimethyl-acetamide (60.0 g, 186 mmol) in toluene (432 g) was added Pd on charcoal (5% Pd, 50% water content, 1.1 mmol). Thereafter MeOH (492 g) was added and the mixture was stirred under an atmosphere of hydrogen (over pressure 0.1 bar) at 45° C. for 2 h. After completion of the reaction the pressure was released, concentrated HCl (36.5%, 22 g, 220 mmol) added and the reaction mixture heated to reflux for further 1 h. The catalyst was filtered off, the pH adjusted with NaOH to 9 and the MeOH distilled off under reduced pressure. After addition of water (200 g) and stirring for 1 h the precipitate was filtered off, washed twice with water (100 g) and dried at 50° C. under reduced pressure. The product was obtained as a tan solid (38.9 g, 90% pure by NMR, 160 mmol, 86% yield).

$^1$H NMR (DMSO-$d_6$, 500 MHz): δ (ppm)=11.9 (bs, 1 H); 7.15 (d, J=11.0 Hz, 1 H); 6.55 (d, J=8.5 Hz, 1 H); 5.28 (bs, 2 H).

$^{13}$C NMR (DMSO-$d_6$, 125 MHz): δ (ppm)=153.7 (t, J=38 Hz); 146.1 (d, J=235 Hz); 133.9 (d, J=15 Hz); 127.3 (d, J=11 Hz); 120.9 (d, J=3 Hz); 113.1 (t, J=260 Hz); 104.9 (d, J=24 Hz); 102.4 (d, J=5 Hz).

3. PREPARATION OF DIAMINO COMPOUNDS OF FORMULA (VII)

Example 3.1

Synthesis of 2,2-difluoro-2-(2,4-diamino-5-fluoro-phenoxy)-N,N-dimethyl-acetamide

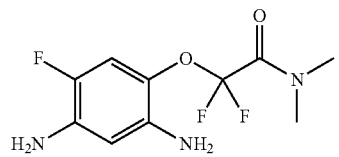 [SMILES: CN(C)C(=O)C(F)(F)Oc1cc(F)c(N)cc1N]

To a solution of 2,2-difluoro-2-(2,4-dinitro-5-fluoro-phenoxy)-N,N-dimethyl-acetamide (22.0 g, 68.1 mmol) in toluene (200 g) obtained according to example 4.1 alternative 2 Pd/C (10% Pd, dry catalyst, 0.7 g, 0.7 mmol) was added. Thereafter, MeOH (80 g) was added and the mixture was stirred under an atmosphere of hydrogen (pressure of 0.1 bar) at 45° C. for 90 min. After completion of the reaction the pressure was released, the catalyst was filtered off and the filtrate was evaporated to dryness. The product (17.3 g, 84% pure by NMR, 55.2 mmol, 81% yield) was obtained as an off-white solid. If desired, the purity can be increased by chromatography (SiO$_2$, cyclohexane/EtOAc mixtures).

$^1$H NMR (DMSO-d$_6$, 500 MHz): δ (ppm)=6.79 (d, J=11.0 Hz, 1 H); 6.16 (d, J=8.5 Hz, 1 H); 4.95 (bs, 2 H); 4.60 (bs, 2 H); 3.19 (s, 3 H); 2.96 (bs, 3 H).

$^{13}$C NMR (DMSO-d$_6$, 125 MHz): δ (ppm)=158.3 (t, J=35 Hz); 141.7 (d, J=278 Hz); 137.6; 134.9 (d, J=14 Hz); 123.9 (d, J=9 Hz); 115.8 (t, J=272 Hz); 109.2 (d, J=22 Hz); 102.0 (d, J=4 Hz); 36.9; 36.2.

4. PREPARATION OF DINITRO COMPOUNDS OF FORMULA (VI-1)

Example 4.1

Synthesis of 2,2-difluoro-2-(2,4-dinitro-5-fluoro-phenoxy)-N,N-dimethyl-acetamide Alternative 1:

To a mixture of H$_2$SO$_4$ (98%, 34.5 g, 345 mmol) and HNO$_3$ (100%, 11.0 g, 175 mmol) at room temperature was added 2,2-difluoro-2-(3-fluoro-phenoxy)-N,N-dimethyl-acetamide (8.7 g, 37 mmol). The temperature rose to 40° C. and was kept at that temperature for further 3 h. The mixture was then poured on 100 g of ice-water. The precipitate was taken up in 50 g of toluene and the aqueous phase was extracted with 25 g of toluene. The combined org. phases were washed with saturated NaHCO$_3$ solution and water. The crude product (11.5 g, 82% purity by quant. HPLC, 29 mmol, 78% yield) was obtained after removal of all volatiles as a yellowish solid. Analytically pure material the crude material could be obtained after recrystallisation from cyclohexane/EtOAc (80:20).

Alternative 2:

A solution of 61.5 g HNO$_3$ (100%, 0.976 mol) and 433.7 g H$_2$SO$_4$ (96%, 4.245 mol) was prepared at 0-20° C. by addition of HNO$_3$ to the sulfuric acid (quantity of mixed acid: 495.2 g). 100 g 2,2-difluoro-2-(3-fluoro-phenoxy)-N,N-dimethyl-acetamide (99%, 0.425 mol) was filled into the reaction vessel at 0° C. 236.9 g of the mixed acid (portion 1) was added at a rate to keep the temperature between 0 and 10° C.

258.3 of the mixed acid (portion 2) was dosed at 40° C. Upon complete addition the mixture was kept at 40° C. for another 9 h. Then, it was cooled to 25° C. and poured to a mixture of 1000 g ice water and 500 ml toluene. Reactor was rinsed with 100 g water and 50 g toluene. The phases were separated at 20° C. The aqueous layer was extracted with 240 g toluene and then discarded. The combined organic layers were washed 4 times with 400 g water in each case (final pH-value of the organic phase: 3). The water in the remaining organic phase was removed by distilling off toluene/water at reduced pressure. The product was obtained as a solution in toluene: 541.3 g (concentration of the dinitro compound by quant. HPLC: 22.3%; yield: 88.1%).

$^1$H NMR (CDCl$_3$, 400 MHz): δ (ppm)=8.82 (d, J=7.5 Hz, 1 H); 7.52 (d, J=11.0 Hz, 1 H); 3.26 (s, 3 H); 3.11 (s, 3 H).

$^{13}$C NMR (CDCl$_3$, 100 MHz): δ (ppm)=157.1 (d, J=276 Hz); 156.7 (d, J=34 Hz); 147.6 (td, J=3 Hz, J=11 Hz); 136.9; 132.9 (d, J=9 Hz); 124.2; 115.3 (t, J=281 Hz); 111.7 (td, J=3 Hz, J=26 Hz); 36.8; 36.7.

Melting point: 66° C.

The invention claimed is:

1. A process for manufacturing 4-propargylated amino-benzoxazinones of formula (I), wherein
R$^1$ is H or halogen;
R$^2$ is halogen;
R$^3$ is H or halogen; and
W is O or S;
comprising
(a) preparing propargyl chloride by reacting propargyl alcohol with thionyl chloride optionally in the presence of a catalyst; and
(b) reacting the propargyl chloride prepared in step (a) with a NH-benzoxazinone of formula (II), or a salt thereof,
optionally in the presence of a base.

2. The process of claim 1, wherein the propargyl chloride prepared in step (a) is used directly in step (b) without further purification.

3. The process of claim 1, wherein in step (a) the thionyl chloride and optionally the catalyst are initially charged in a reaction vessel, if appropriate with the desired solvent, and subsequently the propargyl alcohol is added.

4. The process of claim 1, wherein step (a) is carried out in the presence of a catalyst.

5. The process of claim 1, wherein in step (a) the catalyst is selected from the group consisting of phosphine oxides, guanidinium salts, open-chain and cyclic alkylureas, alkylacetamides and N,N-dialkylformamides.

6. The process of claim 1, wherein in step (a) the catalyst is selected from at least one of formamides of formula (X) or ureas of formula (XI)

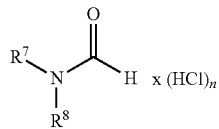
(X)

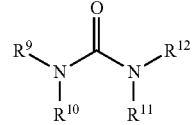
(XI)

wherein
$R^7, R^8, R^9, R^{10}, R^{11}$ and $R^{12}$ independently of one another are $C_1$-$C_6$-alkyl, or
$R^7$ and $R^8$, $R^9$ and $R^{10}$, $R^{10}$ and $R^{11}$, or $R^{11}$ and $R^{12}$ independently of one another together form a $C_4$-$C_5$-alkylene chain, each of which may be interrupted by from 1 to 4 oxygen or nitrogen atoms; and
n has a mean value of from 0 to 3.

7. The process of claim 1, wherein in step (a) the catalyst is selected from at least one urea of formula (XI)

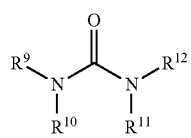
(XI)

wherein
$R^9, R^{10}, R^{11}$ and $R^{12}$ independently of one another are $C_1$-$C_6$-alkyl, or
$R^7$ and $R^8$, $R^9$ and $R^{10}$, $R^{10}$ and $R^{11}$, or $R^{11}$ and $R^{12}$ independently of one another together form a $C_4$-$C_5$-alkylene chain, each of which may be interrupted by from 1 to 4 oxygen or nitrogen atoms.

8. The process of claim 1, wherein step (b) is carried out in the presence of a base.

9. The process of claim 1, wherein the base used in step (b) is selected from the group consisting of carbonates, hydrogen carbonates, hydroxides, oxides, phosphates and alkoxides.

10. The process of claim 9, wherein the base used in step (b) is selected from carbonates.

11. The process of claim 1, wherein $R^1$ and $R^3$ are halogen.

12. The process of claim 1, wherein
$R^2$ is F; and
W is O.

13. The process of claim 1, further comprising the following steps:
a) reacting a dinitro compound of formula (VI-1)

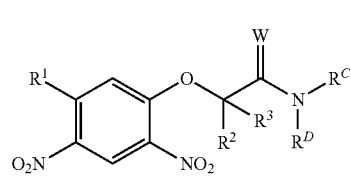
(VI-1)

wherein $R^1, R^2, R^3$ and W are defined as in claim 1; and
$R^C, R^D$ are independently of each other selected from the group consisting of $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl and benzyl, wherein the phenyl and the benzyl ring are independently of one another unsubstituted or substituted by 1 to 5 substituents selected from the group consisting of halogen, $NO_2$, $C_1$-$C_6$-alkyl and $C_1$-$C_6$-alkoxy,
or $R^C$ and $R^D$ together with the N atom which they are attached to, represent a saturated or aromatic 3- to 6-membered ring, optionally containing 1 to 3 additional heteroatoms selected from the group consisting of O, S and N, with the ring optionally being substituted with 1 to 3 $C_1$-$C_6$-alkyl substituents
with a reducing agent to obtain a diamino compound of formula (VII)

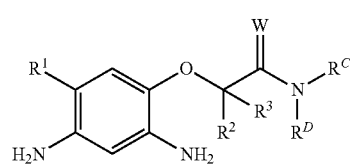
(VII)

wherein $R^1, R^2, R^3$ and W are defined as in claim 1, and $R^C$ and $R^D$ are defined as above;
b) treating the diamino compound of formula (VII) with an acid to obtain an NH-benzoxazinone of formula (II) as defined in claim 1;
c) reacting propargyl alcohol with thionyl chloride to obtain propargyl chloride as defined in claim 1; and
d) reacting the propargyl chloride obtained in step c) with the NH-benzoxazinone of formula (II) obtained in steps a) and b) with a base to obtain a 4-propargylated amino-benzoxazinones of formula (I) as defined in claim 1.

* * * * *